United States Patent [19]

Morrison et al.

[11] Patent Number: 5,332,853
[45] Date of Patent: Jul. 26, 1994

[54] CATALYTIC ALKYLATION PROCESS

[75] Inventors: Robert C. Morrison, Gastonia; Randy W. Hall; B. Troy Dover, both of Kings Mountain; Conrad W. Kamienski, Gastonia; John F. Engel, Belmont, all of N.C.

[73] Assignee: FMC Corporation, Philadelphia, Pa.

[21] Appl. No.: 92,319

[22] Filed: Jul. 14, 1993

Related U.S. Application Data

[60] Continuation-in-part of Ser. No. 842,902, Feb. 27, 1992, abandoned, which is a division of Ser. No. 736,660, Jul. 26, 1991, abandoned.

[51] Int. Cl.$^5$ ............................................. C07F 7/04
[52] U.S. Cl. ............................................. 556/478
[58] Field of Search ................................... 556/478

[56] References Cited

U.S. PATENT DOCUMENTS 3,420,903  1/1969  Smith ........................ 260/665 R
4,593,112  6/1986  Takamizawa ................ 556/480
4,814,474  3/1989  Shirahata .................... 556/477

OTHER PUBLICATIONS

W. Novis Smith, *Journal of Organometallic Chemistry*, 82 pp. 1-6.
A. Shirahata, Tetrahedron Letters, vol. 30, No. 46 pp. 6393-6394.

*Primary Examiner*—Jose' G. Dees
*Assistant Examiner*—Joseph M. Conrad
*Attorney, Agent, or Firm*—Charles C. Fellows; Robert L. Andersen

[57] ABSTRACT

This application concerns a process for alkylating, in a hydrocarbon solvent reaction medium, metalloidal substrates such as alkylating a chlorosilane with an alkyllithium containing 3 to 8 carbon atoms by conducting these reactions in the presence of a catalyst selected from primary and secondary alcohols, and their respective metal alkoxides, cyclic ethers, hydrocarbyl ethers, hydrocarbyl silyl ethers, and tertiary amines.

28 Claims, No Drawings

CATALYTIC ALKYLATION PROCESS

This application is a continuation-in-part of Ser. No. 842,902 filed Feb. 27, 1992 which application was a division of application Ser. No. 736,660 filed Jul. 26, 1991, both abandoned.

The present invention concerns a process for producing alkylated organometalloidal compounds especially organosilanes in high yields by catalyzing the alkylation of metalloidal substrates.

Alkylated chlorosilanes have various uses in organic synthesis reactions. The use of t-butyldimethylchlorosilane as a protecting agent, particularly as an OH-protector, in the manufacture of pharmaceuticals such as antibiotics, carbapenems, prostaglandins and the like is well known.

The reaction of t-butylmagnesium chloride with dichloromethylsilane was disclosed by M. Takamizawa et al in U.S. Pat. No. 4,593,112 to give a 70% yield of t-butylmethylchlorosilane; the latter product is treated with methylmagnesium chloride to yield t-butyldimethylsilane [98%], which is then chlorinated in 85% yield to give t-butyldimethylchlorosilane. The overall yield of this multi-step reaction is low [58%].

It is disclosed by A. Shirahata in Tetrahedron Letters, vol. 30, No. 46, pp. 6393–6394 [1989] that reaction of tertiary butylmagnesium chloride with dimethyldichlorosilane in the presence of cuprous cyanide in THF gives a 74% yield of t-butyldimethylchlorosilane. The yield is low and expensive solvent is used.

The reaction of isopropylmagnesium chloride with trimethylchlorosilane to give isopropyltrimethylsilane [no yield given] is disclosed by A. Shirahata in U.S. Pat. No. 4,818,474. Chlorination of the isopropyltrimethylsilane causes a rearrangement to alpha-chloro-, chloro-, alpha, alpha dimethyl, trimethylsilane [no yield given]. Treatment of the latter compound with aluminum chloride gave the desired t-butyldimethylchlorosilane. Again, a multi-step reaction in low overall yield is projected (expensive solvent).

The present invention provides processes for producing alkylated metalloidal compounds in high yields by alkylation of the metalloidal substrates in a hydrocarbon solvent in the presence of certain catalysts or protocatalysts in a hydrocarbon solvent. These processes are especially useful in alkylations involving bulky or highly hindered alkyl groups such as isopropyl, tertiary butyl, 2-ethylhexyl groups, and the like.

Metalloidal substrates which are alkylated via alkyl-halogen exchange employing alkyllithium compounds are chlorosilanes. These reactions may be exemplified by the reaction sequence:

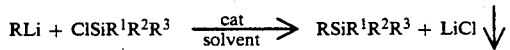

wherein R is an alkyl group and $R^1$, $R^2$, and $R^3$ are independently selected from hydrogen, halogen, and various carbon containing compounds.

One aspect of the present invention provides an improved process for producing alkylated chlorosilanes by reacting an alkyllithium compound with a chlorosilane or an alkyl-substituted chlorosilane in the presence of a small amount of certain organic substances added either to the reactants or to the reaction mixture itself. These organic substances greatly accelerate the reaction and also bring about a more complete reaction, on the order of 95% or so in a period of 2 minutes to 7 hours. The reactions are conducted in a hydrocarbon solvent. These organic substances may be termed catalysts or protocatalysts, that is, substances that are converted into catalysts by reaction with any of the reactants of this invention. Whatever they are termed these organic substances result in a more complete reaction in a shorter period of time and also result in surprisingly less impurities from side reactions.

The catalysts and/or catalyst precursors most useful in the practice of this invention include compounds in several basic categories. One such category includes alcohols, primary and secondary amines and phosphines of the formula

wherein R, $R^1$ and $R^2$ are independently selected from hydrogen, alkyl and alkenyl radicals of 1 to 10 carbon atoms, cycloalkyl radicals of 3 to 10 carbon atoms and aryl radicals of 6 to 18 carbon atoms, $R^3$ is independently selected from alkyl groups containing 1 to 10 carbon atoms and alkylene groups containing 2 to 5 carbon atoms, aryl radicals of 6 to 18 carbon atoms, four to six membered heterocyclic carbon-containing groups containing one to two hetero atoms selected from oxygen, nitrogen, and sulfur, hydroxyalkyl and hydrocarbyloxy groups containing 1 to 10 carbon atoms, alkoxyalkyl groups containing 2 to 13 carbon atoms and mono- and dialkylaminoalkyl groups containing 2 to 13 carbon atoms, $M^a$ is a group IV metal selected from silicon, carbon, germanium and tin, A is selected from oxygen, sulfur, nitrogen and phosphorous, x and y independently have values from zero to two and z has a value of one or two.

Alcohols encompassed by the above Formula (I) can be mono-, di-, or polyhydric, primary and secondary alcohols containing 1 to 10 carbon atoms, which include but are not limited to methanol, ethanol, isopropanol, n-, iso-, and sec-butanol, n-hexanol, n-octanol, 2-methylpentanol, 2-ethylhexanol, cyclohexanol, ethylene glycol and diethylene glycol and their monoethers, glycerol, benzyl alcohol, phenol, thiophenol and the like. Tertiary alcohols, such as t-butanol and 2,3-dimethyl-2-butanol, appear to possess a lesser catalytic activity. Preferred among these alcohols are $C_1$ to $C_8$ non-tertiary alkanols, such as e.g., isopropanol iso- and sec-butanol, 2-methylpentanol, 2-ethylhexanol, and cyclohexanol.

Additional compounds encompassed by Formula (I) include mono- and bis-hydrocarbyl amines containing 1 to 8 carbon atoms such as methylamine, ethylamine, propylamine, sec-butylamine, di-2-ethylhexylamine, diethylamine, N,N'-dimethylethylenediamine and isopropylcyclohexylamine.

Among other substances useful in the practice of this invention, whether they are catalysts, catalyst precursors or protocatalysts, are compounds of the formula

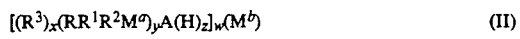

wherein R, $R^1$, $R^2$ are independently selected from hydrogen, alkyl and alkenyl radicals of 1 to 10 carbon atoms, cycloalkyl radicals of 3 to 10 carbon atoms and aryl radicals of 6 to 18 carbon atoms, $R^3$ is selected from alkyl groups containing 1 to 10 carbon atoms and alkylene groups containing 2 to 5 carbon atoms, aryl radicals of 6 to 18 carbon atoms, four to six membered heterocyclic radical groups containing one to two hetero atoms selected from oxygen, nitrogen, and sulfur; hydroxyalkyl, alkoxyalkyl and mono- and dialkylaminoalkyl radicals containing 2 to 13 carbon atoms, $M^a$ is a Group IV element selected from silicon, carbon, germanium and tin, A is selected from oxygen, sulfur, nitrogen and phosphorous, and $M^b$ is selected from lithium, sodium, magnesium, calcium, potassium and zinc; x and y independently have values from zero to two, z is zero or one and w is one or two. These substances, which may hereinafter be termed catalysts, include metal alkoxides, metal alkylamides and imides, metal alkyl phosphides and metal alkylsulfides.

The metal alkoxide catalysts of Formula (II) can be generated from the reaction of alkyllithium compounds with a variety of oxygen containing organic compounds such as alcohols, aldehydes, ketones, esters, carboxylic acids and anhydrides, and the like.

Useful metal alkoxides include, but are not limited to, lithium ethoxide, lithium isopropoxide, lithium benzyloxide, lithium n-octyloxide, lithium cyclohexyloxide, lithium n-hexyloxide, lithium 2-methylpentyloxide, sodium isopropoxide, magnesium 2-methylpentyloxide, zinc isopropoxide, potassium tertamyloxide, lithium trimethylsilanolate and the like and metal alkoxides formed by the reaction of alkyllithium compounds with oxygen. Metal alkoxides which interact with organolithium reagents are also useful, e.g., magnesium, zinc, and calcium alkoxides. Most preferred are lithium alkoxides.

Also included are metal mono- and bis-hydrocarbyl amide and imide compounds of Formula (II) generated by the reaction of organolithium compounds with a variety of nitrogen containing organic compounds such as mono- and dialkylamines, nitriles, carbamates, imines, silylazanes and the like. Examples of metal amides are those selected from the group consisting of lithium n-hexylamide, lithium diisopropylamide, lithium 2-ethylhexylamide, lithium bis-2-ethylhexylamide, lithium diisobutylamide, and lithium hexamethyldisilazane.

The metal mono- and bis-hydrocarbyl phosphide catalysts of Formula (II) are generated by the reaction of organolithium compounds with a variety of phosphorous containing organic compounds including mono- and dialkyl phosphines.

The metal hydrocarbyl sulfide catalysts of Formula (II) are generated by the reaction of organolithium compounds with a variety of sulfur containing organic compounds including mono- and disulfides, and thiols.

Mixtures of the catalysts can be employed with good results.

The compounds of Formula (II) above react with the metalloidal substrates, such as the chlorosilane reactants of this invention to form mixed silylalkyl ethers, amines, and phosphines, which themselves, function as catalysts or protocatalysts to promote the reaction.

For example, in the practice of utilizing lithium isopropoxide as a catalyst in the preparation of t-butyldimethylchlorosilane it was discovered that t-butyldimethylisopropoxysilane was formed. It was found that this latter compound also functioned as a catalyst in promoting the formation of t-butyldimethylchlorosilane (see Table 1).

Other ethers, such as hydrocarbyl ethers, also function as catalysts or protocatalysts in this reaction (see Table 1).

Thus, among substances useful in the practice of this invention, whether they are catalysts, catalyst precursors or protocatalysts are compounds of the formula $$(RR^1R^2M^a)_y A(R^3)_x \quad \text{(III)}$$

wherein R, $R^1$ and $R^2$ are independently selected from hydrogen, halogen, alkyl or alkenyl groups containing one to thirteen carbon atoms cycloalkyl radicals of 3 to 10 carbon atoms and aryl raicals of 6 to 18 carbon atoms. $R^3$ is independently selected from alkyl groups containing 1 to 10 carbon atoms and alkylene groups containing 2 to 5 carbon, aryl groups containing 6 to 18 carbon atoms, four to six membered hetercyclic carbon containing groups containing one to two hetero atoms selected from oxygen, nitrogen and sulfur; hydroxyalkyl and alkoxyalkyl groups containing 2 to 13 carbon atoms and mono and dialkylaminoalkyl containing 2 to 13 carbon atoms; $M^a$ is a Group IV element selected from silicon, carbon, germanium and tin; A is selected from oxygen, sulfur, nitrogen and phosphorus; x+y are equal to the valence of A; x, and y may independently have a value from zero to three. These substances, which may hereinafter be termed catalysts or protocatalysts, include bis-hydrocarbyl ethers, hydrocarbyl silyl ethers, bis-silyl ethers, trishydrocarbylamines, hydrocarbyl silyl amines, trisorganosilyl amines, trisorganogermylphosphines and the like. Some Examples of compounds of Formula III are as follows:

a. Hydrocarbylsilyl and bis-silyl ethers generated by reaction of chlorosilanes with alcohols or metal alkoxides, such as e.g., chlorodimethylisopropoxysilane, t-butyldimethylisopropoxysilane, trimethylisopropoxysilane, dichloromethylisopropoxysilane, and hexamethyldisiloxane.

b. Hydrocarbyl ethers such as, e.g., cyclic and acyclic ethers, symmetrical and unsymmetrical dialkyl, diaryl and alkylaryl ethers which include, but are not limited to, dimethyl ether, diethyl ether, tetrahydrofuran, methyltetrahydrofuran and tetrahydropyran, anisole, methyl-t-butyl ether, di-n-butyl ether, diamyl ether, di-n-hexyl ether, di-n-octyl ether, diphenyl ether and the like. Additional useful ethers are glycol ether types, such as the mono- and di- methyl, ethyl and butyl ethers of ethylene glycol, diethylene glycol, triethylene glycol, and the like. Also useful are acetals (1,1-ethers), such as dimethoxymethane and diethoxymethane. Preferred among these are the dialkyl ethers such as diethyl ether, di-n-octyl ether and methy-t-butyl ether, and most preferred is methyl tert butyl ether.

Although the use of stoichiometric, or greater, amounts of ethers in conjunction with alkyllithiums is known to substantially enhance the latter's reactivity with a number of different substrates, including chlorosilanes, the employment of catalytic quantities in the order of less than 0.05 moles per mole of alkyllithium is not known. The rate enhancement which the presence of these ethers brings to the reaction is totally unexpected. Enhancement factors as high 200 times (see Table 1) have been experienced with the use of as little as one mole percent, based on alkyllithium, of ethers, such as THF and n-octyl ether. On the other hand, we have found that the use of stoichiometric or greater quantities of these ethers in such reactions drastically reduces the yields of desired product obtained (see Table 2), and such quantities of ethers are to be avoided.

c. Tris-hydrocarbylamines such as e.g., cyclic and acyclic tertiary amines including triethylamine, tri-n- butylamine, N, N, N', N'-tetramethylethyleneenediamine (TMEDA), pentamethyldiethylenetriamine, triethylenediamine, N-methylaniline, and the like. Like tertiary phosphines are also useful.

As mentioned above under a description of the catalysts or protocatalysts of Formula II chemical compounds useful in practicing this invention are organic compounds reactable with alkyllithiums to form metal alkoxides, which include alcohols, aldehydes, such as acetaldehyde and benzaldehyde; ketones, such as acetone, acetophenone and benzophenone; esters, such as ethyl acetate, and ethyl benzoate; and carboxylic acids such as acetic and benzoic acids. Preferred among these are $C_1$ to $C_8$ alkyl aldehydes, ketones, esters and carboxylic acids. Also of value are organic compounds such as benzonitrile, acetonitrile, hexanenitrile, N-methylacetamide and the like.

Catalysts and/or catalyst precursors of this invention are also formed by the reaction of alkyllithium compounds with inorganic compounds. For example, water, even in its hydrated form, reacts to form catalysts. Components of air, such as carbon dioxide and oxygen react to form compounds which function as catalysts or catalyst precursors. These catalysts or protocatalysts are less active than some of the organic compound types mentioned above (see Table 1).

The catalysts and or catalyst precursors used to produce organometalloidal compounds can be utilized in various ways. For example, the catalyst or catalyst precursors such as alcohols, metal alkoxides, ethers or silyl ethers can be added:

[a] directly to the reaction mixture;
[b] to the alkyllithium reagent; or
[c] to the chlorosilane reactant.

The alcohols, aldehydes, ketones, esters, carboxylic acids and carboxylic acid anhydrides and other organic compounds can be reacted with an alkyllithium compound to form a metal alkoxide of Formula II, and the resulting metal alkoxide added to the reaction or these organic compounds can be reacted with the alkyllithium in place.

Solvents useful in the process of this invention are preferably liquid hydrocarbons such as saturated aliphatics containing 4 to 8 carbon atoms, saturated cycloaliphatics containing 6 to 9 carbon atoms and aromatics containing 6 to 9 carbon atoms which include, but are not limited to pentane, hexane, heptane, cyclohexane, cumene and toluene.

All reactions should be carried out under an inert atmosphere. The reaction is conveniently and preferably conducted at atmospheric pressure although higher and lower pressures can be employed if desired. Use of higher pressures permit use of propane and butane as solvents. Reaction temperatures can range from 0 to 50 degrees centigrade, and preferably are in the range of 20 to 40 degrees centigrade. This preferred temperature range helps control the amount of impurities formed during reaction. Reactions are sufficiently exothermic employing the catalysts and protocatalysts of this invention so as not to require the supply of added heat which is normally necessary for uncatalyzed reactions.

The mole percent of catalyst employed is generally in the range of 0.01 to 10 mole percent, based on the alkyllithium employed or being formed, with the preferred range being 0.02 to 3.0 mole percent with about one mole percent being most preferred, in the hydrocarbon solvent reaction medium. Use of this lower percentage is an advantage in the recovery and purification of the final product in that little or no by-products resulting from reaction of the metal derivative of the catalyst with the chlorosilane is observed in the desired final product.

As shown in Table 1, the preferred catalysts or catalyst precursors for catalyzing the alkylation of metalloidal substrates are aliphatic primary and secondary alcohols, their metal alkoxides and aliphatic ethers (Formulae I, II, III). However, the operator may choose a substance from the Table on the basis of a desired reaction rate, its boiling range in relation to the desired product, or any number of other factors. For example, in the preparation of t-butyldimethylchlorosilane, a preferred substance is 2-methyl-1-pentanol (2-MPOH), which offers a reasonably fast reaction rate at 20° to 40° C. In addition, the 2-MPOH forms a by-product silyl ether which does not interfere in the purification by distillation from the deposited t-butyl-dimethylchlorosilane.

The relative proportion of reactants can be fairly close to stoichiometric, generally only about 3 mole percent or less of the chlorosilane in excess over the alkyllithium being required. This can be compared with 5 mole percent required in the uncatalyzed reaction. The overall concentration of the product of reaction can be as high as desired, but is generally in the order of about 1 to 2 molar.

Some of the catalyst or catalysts precursors of this invention (see Table 1) accelerate the rate of reaction with metalloidal substrates to such an extent that the process is amenable to continuous, as well as batch, reactors. The yields of products obtained using the preferred catalysts of the invention are generally in the range of at least 90% or more and 90 to 100% when reacting a bulky alkyllithium compound with a chlorosilane. In addition, recoveries of products on distillation of the products of the latter reaction are also higher (90–100%), because of fewer impurities formed [by-products] and lesser chlorosilane reactant needed. The purity of the distilled products is of the order of 99+%.

Silanes useful in the process of this invention can be simple chlorosilanes, $SiCl_xH_{4-x}$, in which x is an integer of from 1 to 4, such as, $SiCl_4$, $SiClH_3$, and $SiCl_2H_2$, alkylchlorosilanes, $R_xSiCl_y$ and mixed types, $R_xSiCl_yH_z$, such as, $RSiCl_3$, $R_2SiCl_2$, $R_3SiCl$, and $R_2SiClH$, where R is a lower alkyl group containing 1 to 4 carbon atoms, but preferably the alkyl group is methyl and ethyl, x is a value of 1 to 3, y and z each has a value of 1 or 2, y +z is equal to 2 or 3 and x+y+z is equal to the valence of silicon.

Organolithium compounds useful in the reactions with organometalloidal substrates have the formula RLi wherein R is an alkyl group containing 3 to 12 carbon atoms which include, but are not limited to, isobutyllithium, sec-butyllithium, tert-butyllithium, neopentyllithium, 2-ethylhexyllithium, n-hexyllithium, n-octyllithium, and iso-propyllithium. Preferably, the alkyllithium compound contains 3 to 6 carbon atoms and is most preferably selected from isopropyllithium, tert-butyllithium, isobutyllithium and sec-butyllithium.

The following Examples further illustrate the invention. Unless indicated otherwise, temperatures are in degrees Centigrade and reactions were done at atmospheric pressure. The reaction rate of conversion was monitored by analyzing a small sample of the reaction mixture by Gas-Liquid Chromatography (GLC) analysis which may be termed simply gas chromatographic analysis.

Final products produced by the process of the invention include, but are not limited to, compounds represented by the formulas $R^1SiCl_3$, $[R^1]_2Si[Cl]_2$, $RR^1SiCl_2$, $R_2R^1SiCl$, $R_3R^1Si$, $R^1SiH_3$, $RR^1SiClH$, and $[R^1]_2SiClH$ and the like wherein R contains 1 to 4 carbon atoms and $R_1$ contains 3 to 12 carbon atoms. Compounds which can be prepared according to this invention include, but are not limited to, compounds such as t-butyldimethylchlorosilane, methyltri-n-octylsilane, di-t-butylsilane, di-t-butyldichlorosilane, and methyl- tert-butylchlorosilane and the like. No special conditions of pressure or stirring are necessary in practicing the process of this invention. All reactions should be carried out under an inert atmosphere.

The following Examples further illustrate the invention. Unless indicated otherwise, all the reactions were conducted under an argon atmosphere using clean, carefully dried equipment, and temperatures are in degrees centigrade.

EXAMPLE 1

Synthesis of t-Butyldimethylchlorosilane Employing Isopropanol as Catalyst

A reactor equipped with a reflux condenser an addition funnel for adding liquid materials to the reactor, a temperature indicating device, and means for stirring the reaction mass, was charged under an argon atmosphere with 0.815 moles of t-butyllithium as a 16 weight percent solution in pentane. The addition funnel was charged with 0.52 grams (0.0086 moles) of isopropyl alcohol which was further diluted with 25 milliliters of pentane. The mixture in the addition funnel was then added dropwise to the solution of t-butyllithium in the reactor. The temperature rose from 21° to 24.2° C. Next, 107.8 grams (0.815 moles) of dimethyldichlorosilane (DMDCS) was charged to the addition funnel and diluted with 110 milliliters of pentane. The temperature of the reaction mass was raised to 34° C., and the mixture in the addition funnel was slowly added (dropwise) to the reaction mass. The reaction mass was again heated to raise the reaction temperature to 35.2° C., and after this heating no further external heating was required. The slow addition of the silane was complete after a total elapsed time of one hour and fifty-five minutes, at which time the reaction temperature was 36.6° C. The reaction was continued with agitation and samples occasionally taken for gas-chromatographic (GC) analysis. The temperature peaked at 37.8° C. after 3 hours and 25 minutes from starting the DMDCS addition. The temperature slowly declined over the next three hours to 30.9° C. The reaction, with slowed agitation, was left overnight at which time the temperature was 23° C., and a sample was removed for GC analysis. Agitation was continued at a temperature of 23° C. for an additional 4 hours and 50 minutes when another sample was taken for GC analysis.

The reaction mass was transferred to a glass filter funnel and filtered to obtain a clear solution. The solid filtration residue was washed with three times with 30 milliliter aliquots of pentane. The washes were combined with the main filtrate obtaining a total weight of solution of 460.1 grams. A total of 114.6 grams (0.76 moles) of t-butyldimethylchlorosilane was obtained by fractional distillation of the final product solution. The recovered yield was 94.3% based on t-butyllithium employed and the purity of the product was 99.65%. Gas chromatographic analyses indicated 90% conversion of dimethyldichlorosilane to t-butyldimethylchlorosilane (TBDMCS) in four hours with 100% conversion in six hours.

EXAMPLE 2

Synthesis t-Butyldimethylchlorosilane Employing Isopropanol as Catalyst-Inverse Addition A reactor slightly larger, but similarly equipped to the reactor in Example 1, was charged (under argon) with 101.6 grams (0.788 moles) of DMDCS and diluted with 110 milliliters of pentane. A preformed solution of lithium isopropoxide (75 milliequivalents) in pentane was added to 290.8 grams (0.741 moles) of t-butyllithium in pentane (16.3 weight percent). The t-butyllithium-lithium isopropoxide mixture was then charged to the addition funnel. The contents of the reactor were heated to 34° C., and a slow dropwise addition of the contents of the addition funnel was started. The reaction mass was agitated continuously during the reaction. After 38 minutes the reaction mass temperature reached 41.8oC, and external heating was ended. Addition of the t-butyllithium-lithium isopropoxide mixture continued for a total period of 3 hours and 10 minutes. The reaction was allowed to continue with agitation for another 24 hours and 5 minutes during which time the reaction mass temperature descended to room temperature (23.4° C.). The reaction was monitored by removing a sample from time to time for GC analysis.

The reaction mass was transferred to a glass filter funnel and filtered. The solid filtration residue was washed three times with 60 ml aliquots of pentane and combined with the main filtrate. A total of 509.6 grams of clear filtrate solution was obtained in 15 minutes. A total of 106.2 grams (0.705 moles) of t-butyldimethylchlorosilane was obtained by fractional distillation of the filtrate. The recovered yield was 95.1% based on t-butyllithium employed and the purity of the distilled product was 99.1%. Gas chromatographic analyses indicated 90% conversion of dimethyldi-chlorosilane to t-butyldimethylchlorosilane 3 hours, and 100% conversion in 5 hours.

EXAMPLE 3

Synthesis TBDMCS Employing 1 Mole percent THF

A reactor similarly equipped to the reactor in Example 1 was charged (under argon) with 131.9 grams (1.02 moles) of DMDCS, 100 milliliters of pentane and 0.813 grams (11.2 millimoles) of tetrahydrofuran (THF). Next, 401 grams of 15.96 weight percent t-butyllithium in pentane (1.00 moles) was charged to the addition funnel. The reaction was begun at a temperature of 17.9° C. by the dropwise addition of t-butyllithium to the reactor. The reaction was exothermic and immediately formed a white precipitate. After 12 minutes of slow feed the reaction temperature had reached 27.6° C., and after 40 minutes time to add about 15% of the total t-butyllithium feed, the reaction had reached a constant reflux (40.2° C.). The reaction mass remained at reflux with no external heating during the remainder of the t-butyllithium feed (2 hours and 55 minutes). GC analysis of a sample taken 5 minutes after completion of the t-butyllithium feed indicated 97.4% conversion of dimethyldichlorosilane to t-butyldimethylchlorosilane. Also indicating complete reaction was the fact that the reflux ceased, and the reaction temperature immediately began to drop after completion of the t-butyllithium feed. The reaction mass was stirred for several more hours.

The reaction mass was transferred to a glass filter funnel and filtered. The solid filtration residue was washed four times with 50 ml aliquots of pentane and combined with the main filtrate. A total of 465.6 grams of clear filtrate was obtained in 20 minutes. A total of 128.7 grams of t-butyldimethylchlorosilane was obtained by fractional distillation of the filtrate. The recovered yield was 85.4% based on t-butyllithium employed, and the purity of the distilled product was 98.9%. Gas chromatographic analyses indicated about 100% conversion of dimethyldichlorosilane to t-butyldimethylchlorosilane in 3 hours which was almost equal to the t-butyllithium feed rate.

EXAMPLE 4

Synthesis TBDMCS Employing 1 Mole Percent Di-n-hexyl Ether

Example 3 was repeated except 2.23 grams di-n-hexyl ether (11.9 millimoles), 124.0 grams dimethyldichlorosilane (0,960 moles) and 150 ml pentane were charged to the reactor and 397.9 grams of 15.19 wt. % t-butyllithium (0.944 moles) was charged to the addition funnel. Fractional distillation of the filtered final product yielded 129.3 grams of t-butyldimethylchlorosilane which represented a 90.9% recovered yield based on t-butyllithium employed. Gas chromatographic analyses indicated 100% conversion of dimethyldichlorosilane to t-butyldimethylchlorosilane in less than 4 hours. Again, conversion was rapid and almost equal to the t-butyllithium feed rate (3 hours and 21 minutes). Purity of the distilled product was 99.6%.

EXAMPLE 5

Catalyst Screening Procedure

The catalyst screening or evaluation procedure involved setting up a t-butyldimethylchlorosilane synthesis reaction which employed no catalyst. Samples were periodically taken from the reaction mass for GLC analysis in order to determine the rate of conversion of dichlorodimethylsilane to t-butyldimethylchlorosilane. Once analyzed, small amounts of potential catalysts or catalyst precursors (usually 1 to 3 mole % based on t-butyllithium) were added to each sample. These samples were also analyzed periodically by GLC in order to determine relative conversion rates as compared to the non-catalyzed reaction. Usually, in this manner, four or five candidate catalytic compounds could be evaluated in a day.

A reactor slightly smaller, but similarly equipped to the reactor in Example 1 was charged with 50 milliliters of 12.7 wt. % t-butyllithium in pentane (0,066 moles) and 9.6 grams of dichlorodimethylsilane (0,074 moles). The reaction mass was agitated continuously during the reaction but, was not heated. After 25 minutes, 2 milliliters of the reaction mass was transferred via syringe to a pre-dried and argon purged 5 ml serum bottle which was capped with a rubber septum. One microliter of solution was taken from the bottle for GLC analysis and then a potential catalyst (e.g., 0.07 millimole water) was added to the contents of the bottle via microliter syringe. From time to time the contents of the serum bottle were analyzed by GLC to determine the affect of the additive on the rate of conversion. This procedure was repeated many times with various hydrocarbon solvent reaction media, and candidate catalysts or protocatalysts. Each reaction was monitored by GLC and compared to the non-catalyzed reaction.

The results of the catalyst screening were calculated in terms of relative rates of conversion versus non-catalyzed reactions; these data and the identification of the compounds evaluated are presented in Table 1.

EXAMPLE 6

Synthesis t-Butyltrichlorosilane Employing Di-n-Hexyl Ether (0.05 Mole%) as Catalyst A reactor similarly equipped to the reactor described in Example 1 was charged with 603.3 grams (3.55 moles) of silicon tetrachloride and 150 ml hexane. Next, 1258 grams of t-butyllithium (3.47 moles) in pentane was charged to the addition funnel. The reaction was begun at room temperature (23.8° C.) by the slow addition of t-butyllithium to the reactor. The temperature quickly rose to 29.6° C. due to the moisture content of the silicon tetrachloride and then began to drop. Further addition of t-butyllithium failed to raise the temperature indicating to the slowness of reaction. The reaction mass was heated to 53.7° C. (reflux) as the t-butyllithium was being continually added. Heating was continued for the next hour at which time about 11% of the total t-butyllithium charge had been fed. At the elevated temperature, the reaction rate was still slow as evidenced by the need for heat in order to maintain reflux. The t-butyllithium feed and heating was stopped and the reaction mass was allowed to cool to just below reflux (50.8° C.). Then, 0.4 ml (1.5 millimoles) of di-n-hexyl ether (DHE) was added to the contents of the reactor. The temperature of the reaction mass immediately rose to reflux temperature (51.5° C.) and reflux continued for the next 27 minutes. The remaining t-butyllithium was fed (dropwise) over the next 9 hours and 49 minutes. During this time, the reaction rate was nearly equal to the t-butyllithium feed rate with reaction requiring no added heat to sustain a reflux. However, when the t-butyllithium feed was stopped the temperature quickly dropped and the reflux subsided. The faster reaction rate can be attributed to the small amount of DHE catalyst (0,043 mole% based on t-butyllithium employed). The reaction mass was allowed to cool and stand overnight with no stirring. The reaction mass was transferred to a glass filtration funnel and filtered to remove solid lithium chloride. The solid filtration residue was washed four times with 100 ml aliquots of pentane and which were combined with the main filtrate. A total of 1811.9 grams of clear filtrate was obtained in 8 minutes. A total of 631.6 grams of t-butyltrichlorosilane was obtained by fractional distillation. The recovered (isolated) yield was 95% based on the amount of t-butyllithium employed and the purity of the distilled product was 99.7%.

COMPARISON EXAMPLES

A. t-Butyldimethylchlorosilane Synthesis Employing No Catalyst

A comparison experiment employing no catalyst was also carried out. A reactor similarly equipped to the reactor described in Example 1 was charged (under argon) with 54.9 grams (0,425 moles) of DMDCS and 75 milliliters of pentane. Next, 124.8 grams of a 20.7 wt. % solution of t-butyllithium in pentane (0,403 moles) was charged to the addition funnel. The contents of the reactor were preheated to 36° C., and a slow addition of t-butyllithium was begun. Heating was continued for the next 7 hours in order to maintain the reaction temperature between 38 and 41° C. The reaction mass was continuously agitated during the reaction. Addition of the t-butyllithium was completed in 2 hours and 23 minutes. The reaction was allowed to continue for 141 additional hours with agitation and no heating. The reaction was monitored by removing a sample from time to time for gc analysis.

The reaction mass was transferred to a glass filter funnel and filtered. The solid filtration residue was washed twice with 100 milliliter aliquots of pentane. GLC analysis indicated a 95.6% yield of t-butyldimethylchlorosilane. Gas chromatographic analyses indicated 90% conversion of dimethyldichlorosilane to t-butyldimethylchlorosilane in 70 hours and 100% conversion in 148 hours.

B.-D. t-Butyldimethylchlorosilane Syntheses Employing Large Amounts of Ether Example 5 was repeated several times except large amounts of ethers (ether/t-butyllithium mole ratio range=1 to 3.6) were employed. The reagents employed and results are presented in Table 5:

The filtration residue in each experiment contained a silicon polymer which accounted for yield loss. Thus, the use of stoichiometric or greater amounts of ethers greatly reduces the yield of TBSCL; whereas, employment of catalytic amounts of ethers, unexpectedly result in higher yields, and greatly accelerates the reaction.

E. t-Butyltrichlorosilane Synthesis Employing No Catalyst

A comparison synthesis of t-butyltrichlorosilane employing no catalyst was carried out. A reactor similarly equipped to the reactor described in Example 1 was charged (under argon) with 181.98 grams (1.07 moles) of silicon tetrachloride and 200 ml hexane. Next 328 grams of a 20.3 wt.% solution of t-butyl-lithium in pentane (1.04 moles) was charged to the addition funnel. The reaction was begun by adding 75 ml t-butyllithium to the stirred contents of the reactor. The reaction was very slow as evidenced by only a slight rise in temperature (24.0 to 25.7° C.) in 2 hours and the appearance of little or no lithium chloride. The contents of the reactor were then heated to reflux (57.3° C.) and after 16 minutes the reaction mass began to slowly become cloudy with lithium chloride indicating at least some reaction. The remaining t-butyllithium solution was added over a period of 3 hours and 2 minutes while heating to maintain the reaction temperature at a steady reflux. The reaction mass was heated (reflux) for several additional hours and then left stirring over the weekend. Active carbon lithium analysis of the reaction mass indicated that no t-butyllithium remained at this time.

The reaction mass was transferred to a glass filter funnel and filtered to remove solid lithium chloride. A total of 638.3 grams of a clear light yellow solution was obtained by filtration. Fractional distillation of the filtrate yielded 124.3 grams (0.649 moles) of t-butyltrichlorosilane. The recovered yield was 62.4% based on the amount of t-butyllithium employed. The purity of the main cut was 98.9%.

TABLE 1

| COMPOUND(1) | CATALYST SCREENING RESULTS | | | |
|---|---|---|---|---|
| | CHANGE(2) % | TIME(3) min | % (4) | CHANGE/MIN RELATIVE(5) |
| Ethyl Ether | 74 | 4 | 18.50 | 264 |
| Amyl Ether | 73 | 4 | 18.25 | 261 |
| TMEDA | 78 | 4 | 16.25 | 232 |
| THF (1 mole %) | 78 | 5 | 15.60 | 223 |
| t-Butyl Methyl Ether | 78 | 5 | 15.60 | 223 |
| Diethoxymethane | 78 | 5 | 15.60 | 223 |
| Dimethoxyethane | 77 | 5 | 15.40 | 220 |
| Di-n-hexyl ether | 70 | 5 | 14.00 | 200 |
| Di-n-octyl ether | 63 | 5 | 12.60 | 180 |
| Di-n-butyl ether | 61 | 5 | 12.20 | 174 |
| Cyclohexanol | 72 | 10 | 7.20 | 103 |
| Butoxytriglycol | 70 | 15 | 4.66 | 66 |
| Isopropanol (3 mole %) | 75 | 20 | 3.75 | 54 |
| Ethanol | 81 | 30 | 2.70 | 39 |
| Triethylamine | 69 | 84 | 0.82 | 12 |
| Benzyl Alcohol | 81 | 108 | 0.75 | 11 |
| Acetonitrile | 76 | 180 | 0.42 | 6 |
| CDMIS (9) | 76 | 147 | 0.42 | 7 |
| Anisole | 76 | 185 | 0.41 | 6 |
| Hexanenitrile | 78 | 195 | 0.40 | 6 |
| Acetophenone | 80 | 200 | 0.40 | 6 |
| 3-Heptanone | 80 | 210 | 0.38 | 5 |
| n-Heptaldehyde | 72 | 190 | 0.38 | 5 |
| Carbon Dioxide | 52 | 140 | 0.37 | 5 |
| Water | 81 | 220 | 0.37 | 5 |
| TBDMIS(6) | 80 | 230 | 0.35 | 5 |
| Ethylene Glycol | 63 | 210 | 0.30 | 4 |
| 2-MPOH(7) (1 mole %) | 90 | 310 | 0.29 | 4 |
| Mg(2-MPO)₂ | 71 | 240 | 0.30 | 4 |
| Diphenyl ether | 66 | 240 | 0.28 | 4 |
| Acetic Acid | 73 | 275 | 0.27 | 4 |
| Isopropanol (1 mole %) | 90 | 360 | 0.25 | 4 |
| Air (10 mole %) | 59 | 250 | 0.24 | 3 |

TABLE 1-continued
CATALYST SCREENING RESULTS

| COMPOUND(1) | CHANGE(2) % | TIME(3) min | % (4) | CHANGE/MIN RELATIVE(5) |
|---|---|---|---|---|
| Hexamethyl-disiloxane | 58 | 255 | 0.23 | 3 |
| N-Methyl-acetamide | 50 | 220 | 0.23 | 3 |
| 2,3-Dimethyl-2-butanol | 78 | 405 | 0.19 | 3 |
| n-Hexylamine | 77 | 420 | 0.18 | 3 |
| Thiophenol | 64 | 365 | 0.18 | 3 |
| Benzonitrile | 67 | 420 | 0.16 | 2 |
| N-Methylaniline | 78 | 500 | 0.16 | 2 |
| Potassium t-butoxide | 78 | 720 | 0.16 | 2 |
| t-butanol (6 mole %) | 66 | 555 | 0.12 | 2 |
| Dodecane(8) (blank) | 81 | 936 | 0.09 | 1 |
| None (standard) | 70 | 960 | 0.07 | 1 |

(1) Employed 3 mole % (based on t-butyllithium) unless otherwise noted.
(2) Percent change from when compound was added to the reaction mixture until 90% conversion of dimethyl- di-chlorosilane to t-butyldimethylchlorosilane had occurred.
(3) Period of time in minutes to reach 90% conversion.
(4) $\% = \frac{\% \text{ Change}}{\text{Minutes}}$ (5) Relative rate = $\frac{\text{Catalyst \% Change/Minute}}{\text{Standard \% Change/Minute}}$ (6) t-Butyldimethylisopropoxysilane
(7) 2-Methyl-1-pentanol
(8) Dodecane, an unreactive hydrocarbon, was employed as a blank to determine the effect of transferring and addition of ingredients into the serum bottle.
(9) Chlorodimethylisopropoxysilane

TABLE 2
SYNTHESES t-BUTYLDIMETHYLCHLOROSILANE (TBSCL) EMPLOYING VARIOUS AMOUNTS OF ETHERS

| Example Number | t-BuLi moles | DMDCS[1] moles | Ether type | Ether moles | TBSCL[2] Yield % |
|---|---|---|---|---|---|
| B[6] | 0.103 | 0.103 | THF[3] | 0.3690 | 16.3 |
| C | 0.103 | 0.103 | THF | 0.103 | 34.2 |
| 5 | 1.00 | 1.02 | THF | 0.0112 | 97.8 |
| D | 0.103 | 0.103 | DOE[4] | 0.103 | 65.9 |
| 6 | 0.944 | 0.960 | DHE[5] | 0.0119 | 100 |
| 8 | 3.47 | 3.55 | DHE | 0.05 | 100[7] |

[1] Dimethyldichlorosilane
[2] Yield determined by GLC
[3] Tetrahydrofuran
[4] Di-n-Octyl ether
[5] Di-n-Hexyl ether. In the screening procedure (see Table 1) the relative rates of DOE and DHE were essentially the same.
[6] Examples B, C, and D are Comparison Examples.
[7] t-Butyltrichlorosilane

What is claimed is:

1. A catalytic process for alkylating chlorosilanes by reacting an alkyllithium compound of the formula RLi wherein R is an alkyl group containing 1 to 20 carbon atoms with a chlorosilane comprising conducting the reaction in a hydrocarbon solvent in the presence of 0.01 to 10 mole percent, based on alkyllithium of a catalytic compound selected from the group consisting of (A) a compound represented by the formula $$(R^3)_x(RR^1R^2M^a)_yA(H)_z \qquad (I)$$

wherein R, $R^1$ and $R^2$ are independently selected from hydrogen, alkyl and alkenyl groups containing 1 to 13 carbon atoms, cycloalkyl groups containing 3 to 10 carbon atoms, aryl groups containing 6 to 18 carbon atoms, $R^3$ is independently selected from aryl groups containing 6 to 18 carbon atoms, four to six-membered heterocyclic carbon containing groups containing one to two hetero atoms selected from oxygen, nitrogen, and sulfur; hydroxyalkyl, alkoxyalkyl, and mono- and dialkylaminoalkyl groups containing 2 to 13 carbon atoms, $M^a$ is a group iv metal selected from silicon, carbon, germanium and tin, A is selected from oxygen, sulfur and nitrogen, x and y independently have values from zero to two and z has a value of one or two (B) a compound represented by the formula $$[(R^3)_x(RR^1R^2M^a)_yA(H)_z]_wM^b \qquad (II)$$

wherein R, $R^1$ and $R^2$ are independently selected from hydrogen, alkyl and alkenyl groups containing 1 to 13 carbon atoms, cycloalkyl groups containing 3 to 10 carbon atoms, aryl groups containing 6 to 18 carbon atoms, $R^3$ is independently selected from alkyl groups containing 1 to 10 carbon atoms and alkylene groups containing 2 to 5 carbon atoms, aryl groups containing 6 to 18 carbon atoms, four to six-membered heterocyclic carbon containing groups containing one to two hetero atoms selected from oxygen, nitrogen, and sulfur; hydroxyalkyl groups and alkoxyalkyl groups containing 2 to 13 carbon atoms and mono- and dialkylaminoalkyl groups containing 2 to 13 carbon atoms; $M^a$ is a group iv metal selected from silicon, carbon, germanium, and tin; A is selected from oxygen, sulfur and nitrogen; $M^b$ is selected from lithium, sodium, potassium and magnesium; x and y independently have values from zero to two and z has a value of zero or one and w has a value of 1 or 2;

(C) a compound represented by the formula $$(RR^1R^2M^a)_yA(R^3)_x \qquad (III)$$

wherein R, $R^1$ and $R^2$ are independently selected from hydrogen, halogen, alkyl and alkenyl groups containing 1 to 13 carbon atoms, cycloalkyl groups containing 3 to 10 carbon atoms, aryl groups containing 6 to 18 carbon atoms, $R^3$ is independently selected from alkyl groups containing 1 to 10 carbon atoms and alkylene groups containing 2 to 5 carbon atoms aryl groups containing 6 to 18 carbon atoms, four to six-membered heterocyclic carbon containing groups containing one to two hetero atoms selected from oxygen, nitrogen, and sulfur; hydroxyalkyl groups and alkoxyalkyl groups containing 2 to 13 carbon atoms and mono- and dialkylaminoalkyl groups containing 2 to 13 carbon atoms; $M^a$ is selected from silicon, carbon, germanium, and tin, A is selected from oxygen, sulfur and nitrogen, and x and y independently have values from zero to three, and;

(D) mixtures of (A), (B), and (C) above.

2. The process of claim 1 wherein the chlorosilane is selected from compounds of the formula $R_xSiCl_yH_z$ wherein R is an alkyl group containing 1 to 20 carbon atoms, x and z independently have values from zero to three, and y has a value from one to four.

3. The process of claim 2 wherein the compound of the formula $R_xSiCl_yH_z$ is selected from compounds of the formula $SiCl_4$, $SiHCl_3$, $SiH_2Cl_2$, $RSiCl_3 RSiHCl_2$, $R_2SiCl_2$ and $R_3SiCl$.

4. The process of claim 1 wherein the compound of Formula I

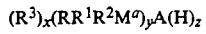   (I)

is an alcohol wherein R, $R^1$, $R^2$ and $R^3$ are defined as in claim 1, $M^a$ is carbon, A is oxygen, z is one, y is one, and x is one.

5. The process of claim 4 wherein the alcohol is selected from the group consisting of methanol, ethanol, isopropanol, n-butanol, isobutanol, sec-butanol, n-hexanol, n-octanol, 2-methylpentanol, 2-ethylhexanol, cyclohexanol, ethylene glycol, and diethylene glycol and their monoethers, glycerol, benzyl alcohol, phenol, and thiophenol.

6. The process of claim 1 wherein the compound of Formula I

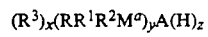   (I)

is a mono- or dihydrocarbyl amine wherein R, $R^1$ $R^2$ and $R^3$ are defined as in claim 1, $M^a$ is carbon, A is nitrogen, y is one or two, z is 1 or 2, and x is zero.

7. The process of claim 6 wherein the mono- or bis-hydrocarbyl amine is selected from the group consisting of methylamine, ethylamine, propylamine, secbutylamine, di-2-ethyl-hexylamine, diethylamine, and N,N'-dimethylethylenediamine, and isopropylcyclohexylamine.

8. The process of claim 1 wherein the compound of Formula II

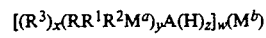   (II)

is a metal alkoxide wherein $M^a$ is selected from silicon, carbon, germanium and tin, A is oxygen, $M^b$ is selected from lithium, sodium or potassium; x and y independently have values from zero to two, z has a value of zero or one, and w has a value of 1 or 2.

9. The process of claim 8 wherein the metal alkoxide is selected from the group consisting of lithium ethoxide, lithium isopropoxide, lithium 2-methylpentyloxide, lithium n-octyloxide, lithium cyclohexyloxide, lithium n-hexyloxide, and lithium benzyloxide.

10. The process of claim 8 wherein the metal alkoxide is formed in place by the reaction of an alkyl-lithium of the formula RLi wherein R is an alkyl group containing 1 to 20 carbon atoms with an organic compound containing 1 to 20 carbon atoms selected from the group consisting of aldehydes, ketones, esters, carboxylic acids, carboxylic acid anhydrides and ethers.

11. The process of claim 10 wherein the organic compound is selected from the group consisting of acetaldehyde, benzaldehyde, acetone, acetophenone, benzophenone, ethyl acetate, ethyl benzoate, acetic acid and benzoic acid.

12. The process of claim 8 wherein $M^a$ is lithium and $R^3$ is an alkoxyalkyl group derived from methoxyethanol, methoxyethoxyethanol, ethoxyethanol, ethoxyethoxy- ethanol and butoxyethoxyethanol.

13. The process of claim 1 wherein the compound of Formula II

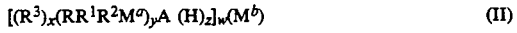   (II)

is a mono- or bis-alkylamide wherein R, $R^1$, $R^2$ and $R^3$ are defined as in claim 1, $M^a$ is a Group IV metal selected from silicon, carbon, germanium and tin; A is nitrogen; $M^b$ is selected from lithium, sodium, potassium and magnesium; x is one or two, y is zero, z has a value of zero or one, and w has a value of one or two.

14. The process of claim 13 wherein the compound of Formula II is a metal mono- or bis-hydrocarbylamide selected from the group consisting of lithium n-hexylamide, lithium diisopropylamide, lithium 2-ethylhexylamide, lithium bis-2-ethylhexylamide, lithium diisobutylamide and lithium hexamethyldisilazane.

15. The process of claim 1 wherein the compound of Formula III is a hydrocarbyl ether wherein R, $R^1$, $R^2$ and $R_3$ are defined as in claim 1, $M_a$ is carbon, A is oxygen, and x+y is two.

16. The process of claim 15 wherein the hydrocarbyl ether is selected from the group consisting of diethyl ether, dimethyl ether, methyl-t-butyl ether, dibutyl ether, diamyl ether, di-n-hexyl ether, di-n-octyl ether, and the dimethyl ether of diethylene glycol.

17. The process of claim 16 wherein the hydrocarbyl ether is selected from diethyl ether, di-n-octyl ether and methyl-t-butyl ether.

18. The process of claim 16 wherein the hydrocarbyl ether is methyl-t-butyl ether, 19. The process of claim 1 wherein the compound of Formula III

   (III)

is a cyclic ether wherein A is oxygen and $R^3$ is a tetramethylene radical.

20. The process of claim 19 wherein the cyclic ether is selected from the group consisting of tetrahydrofuran and methyltetrahydrofuran, and tetrahydropyran.

21. The process of claim 1 wherein R, $R^1$, $R^2$ and $R^3$ are defined as in claim 1, the compound of Formula III

   (III)

is a tris-hydrocarbylamine, wherein $M^a$ is carbon, A is nitrogen, and x+y is three.

22. The process of claim 21 wherein the trishydrocarbylamine is selected from the group of triethylamine, tributylamine, trihexylamine, trimethylamine, methyldibutylamine, tetramethylethylenediamine, and pentamethylethylenetriamine.

23. The process of claim 1 wherein R, $R^1$, $R^2$ and $R^3$ are defined in claim 1, the compound of Formula III:

$$(RR^1R^2M^a)_yA(R^3)_x \qquad (III)$$

is a mixed hydrocarbylsilyl ether wherein $M^a$ is silicon, A is oxygen, and x and y are one.

24. The process of claim 23 wherein the hydrocarbylsilyl ether is selected from the group consisting of chlorodimethylisopropoxysilane, trimethylisopropoxysilane, methyldichloroisopropoxysilane and t-butyldimethylisopropoxysilane.

25. The process of claim 1 wherein the compound of Formula III is a bis-organosilyl ether wherein $M^a$ is silicon, A is oxygen, x is zero and y is two.

26. The process of claim 1 wherein the catalytic compound is present in an amount ranging from 0.1 to 3 mole percent based on the amount of alkyllithium.

27. The process of claim 1 wherein the reaction is maintained at temperatures between −76° and 50° C.

28. The process of claim 1 wherein the reaction is maintained at temperatures between 20° and 40° C.

* * * * *